US007910899B2

(12) United States Patent
Platsch

(10) Patent No.: US 7,910,899 B2
(45) Date of Patent: Mar. 22, 2011

(54) FLAT UV LIGHT SOURCE

(75) Inventor: Hans G. Platsch, Stuttgart (DE)

(73) Assignee: Platsch GmbH & Co. KG, Stuttgart (DE)

( * ) Notice: Subject to any disclaimer, the term of this patent is extended or adjusted under 35 U.S.C. 154(b) by 580 days.

(21) Appl. No.: 11/547,439

(22) PCT Filed: Mar. 29, 2005

(86) PCT No.: PCT/EP2005/003268

§ 371 (c)(1), (2), (4) Date: Mar. 11, 2008

(87) PCT Pub. No.: WO2005/093858

PCT Pub. Date: Oct. 6, 2005

(65) Prior Publication Data

US 2008/0315132 A1 Dec. 25, 2008

(30) Foreign Application Priority Data

Mar. 29, 2004 (DE) ......................... 10 2004 015 700

(51) Int. Cl.
*A61N 5/06* (2006.01)
*G01J 3/10* (2006.01)
*H05G 1/00* (2006.01)

(52) U.S. Cl. ................... 250/504 R; 422/186.3; 438/26; 438/106; 438/118; 438/119; 438/125; 438/126; 588/204; 257/88; 257/91; 257/98; 257/99; 257/100; 362/23

(58) Field of Classification Search .............. 250/504 R; 422/186.3; 438/26, 106, 118, 119, 125, 126; 257/88, 91, 98–100; 362/23
See application file for complete search history.

(56) References Cited

U.S. PATENT DOCUMENTS

| | | | | |
|---|---|---|---|---|
| 3,994,073 A * | 11/1976 | Lackore | .......................... | 34/277 |
| 4,718,163 A * | 1/1988 | Berland et al. | .................. | 29/837 |
| 5,105,429 A | 4/1992 | Mundinger et al. | | |
| 5,936,353 A | 8/1999 | Triner et al. | | |
| 6,078,713 A | 6/2000 | Tausch et al. | | |
| 6,373,188 B1 | 4/2002 | Johnson et al. | | |
| 6,380,962 B1 | 4/2002 | Miyazaki | | |
| 6,849,308 B1 | 2/2005 | Speakman et al. | | |
| 2003/0026096 A1 | 2/2003 | Ellens et al. | | |
| 2003/0160256 A1 | 8/2003 | Durocher et al. | | |
| 2003/0170151 A1* | 9/2003 | Hunter et al. | .............. | 422/186.3 |

FOREIGN PATENT DOCUMENTS

| | | |
|---|---|---|
| DE | 19741585 | 9/1997 |
| DE | 10234076 | 7/2002 |
| WO | 01/11426 | 2/2001 |

* cited by examiner

*Primary Examiner* — Jack I Berman
*Assistant Examiner* — Meenakshi S Sahu
(74) *Attorney, Agent, or Firm* — Factor & Lake, Ltd.

(57) ABSTRACT

A flat UV light source has a tight packing of UV light-emitting diodes (56) that are arranged in a matrix. These light-emitting diodes are cooled by cooling air flows (66) or by cooling water flows.

65 Claims, 14 Drawing Sheets

FLAT UV LIGHT SOURCE

RELATED APPLICATION

This application claims the filing benefit of PCT Patent Application No. PCT/EP2005/003268, filed Mar. 29, 2005; which claims the benefit of German Patent Application No. 10 2004 015 700.6, filed Mar. 29, 2004; the contents of which all are incorporated herein by reference.

TECHNICAL FIELD

The invention relates to a flat UV light source with a supporting structure and with a plurality of UV light-emitting elements supported said supporting structure, characterised in that the UV light-emitting elements are light-emitting diodes and are arranged in a matrix.

BACKGROUND OF THE INVENTION

Flat UV light sources are used, inter alia, in the print industry, in order to dry UV-curable printing-inks. Dryers of such a type encompass mercury-vapour lamps. For the purpose of operating mercury-vapour lamps of such a type, expensive and bulky mains power packs are necessary, which have to provide a high igniting voltage a maintaining voltage. Mains power packs of such a type typically include large choking coils and capacitors.

Furthermore, flat UV light sources are known that are used in sunbeds, for example. They include a plurality of tubular discharge lamps extending parallel to one another. However, with such flat UV light sources the radiation intensity that are necessary for industrial purposes, in particular for the drying of UV printing-inks, cannot be generated.

SUMMARY OF THE INVENTION

In the meantime, UV-emitting light-emitting diodes (UV LEDs) have come into existence. By means of the present invention a flat UV light source is to be created on the basis of UV LEDs of such a type.

This object may be achieved, according to the invention, by means of an UV light source having a supporting structure and with a plurality of UV light-emitting elements supporting said supporting structure, wherein the UV light-emitting elements are light-emitting diodes and are arranged in a matrix.

A further development of the invention includes a light-source wherein the light-emitting diodes are arranged in a densely packed manner, which is advantageous with regard to attaining a high radiation density and with regard to uniformity of the radiation field that is generated.

With the further development of the invention, the light-emitting diodes of the light-source are each arranged downstream of an aperture in a mirror, wherein a further homogenisation of the radiation field is achieved.

Further developments of the invention include the mirror exhibiting scattering surface irregularities, wherein the scattering unit exhibits scattering elements situated upstream of the apertures in the mirror, which provides for homogenisation of the energy density in the radiation field.

Further developments of the invention include the mirror exhibiting scattering surface irregularities, wherein a scattering of UV light is obtained. The mirror may further exhibit dished or domed surface sections, wherein surface sections situated between the apertures in the mirror are convexly curved, such that a homogenisation is obtained by means of small convex or concave collecting mirrors. In this connection, the focal length of said mirrors is so chosen that the focal point is far removed from the plane of the surface to be illuminated, so that also the concave mirror in effect brings about an expansion of a partial light bundle that is incident thereon.

Typically, light-emitting diodes have the highest radiation density on their axis. Therefore, a further development of the invention includes a light-source characterised by a scattering unit arranged upstream of the light-emitting diodes wherein a smearing of the energy from the axis of an LED into the spatial regions spaced from the axis is obtained.

Further developments of the invention include a light-source characterised in that the scattering unit exhibits scattering elements situated upstream of the apertures in the mirror, wherein the relocating of energy from the beam axis to other spatial regions is effected purposefully by means of scattering elements arranged upstream of the LEDs on the axis thereof. These scattering elements may exhibit, for example, partial reflective coatings, the reduction of which in the radial direction is so chosen in that the scattering element exhibits diminishing scattering power with increasing spacing from the axis of the assigned light-emitting diode thereby taking the radiation characteristic of the LEDs into account, wherein substantially the same energy density is obtained downstream of the scattering element.

For many intended uses it is advantageous to perform a UV treatment with different wavelengths, for example in order firstly only to begin to dry a printing-ink and then to cure it fully in volume, or in order to activate various initiators. As such, even further developments of the invention include a light-source characterised in that the light-emitting diodes include varying operating wavelength.

In this connection, the further development of the invention includes a light-source characterised in that the light-emitting diodes are arranged in consecutive rows. It is guaranteed that when use is made of the UV light source for the purpose of treating moving workpieces the surface regions of the workpiece situated transversely in relation to the direction of motion are subjected to UV radiation in like manner.

In this connection, further developments of the invention include a light-source characterised in that the light-emitting diodes of consecutive rows are offset in relation to one another, preferably offset by half a separation in relation to one another in order to guarantee that no 'streaks' arise overall in a moving workpiece, since the points of least energy density of an LED row are in alignment with the points of greatest energy density of the adjacent LED rows in the direction of transport of the workpieces.

Further developments of the invention include a light-source characterised in that a wall supporting the light-emitting diodes exhibits cooling-air apertures that are in communication with a source of cooling air and are situated in the vicinity of the light-emitting diodes in order to guarantee that the heat loss arising at the LEDs can be dissipated well.

In this connection, a further development of the invention includes a light-source characterised in that the cooling-air apertures are in communication with a distribution chamber which is delimited by a rear wall and by a front wall supporting the light-emitting diodes to provide for an identical cooling of the various LEDs of the matrix.

The further development of the invention includes a light-source characterised in that the front wall exhibits cooling-air slots extending parallel to one another, the width of which is comparable to the dimension of a light-emitting diode, and in that further light-emitting diodes that are in alignment with the cooling-air slots are provided downstream of the front wall to permit wide cooling-air slots to be provided between rows of consecutive adjacent LEDs, but it is nevertheless guaranteed that the same UV radiation density is achieved also in the corresponding regions of the treatment surface, since the rear LEDs emit their radiation through the cooling-air slots.

The further development of the invention includes a light-source characterised in that the distribution chamber has cooling air applied to it via supply slots that are in communication with cooling-air channels which serve for a uniform provision of cooling air to the various cooling-air slots, and hence for a uniform cooling of the various LEDs.

The further development of the invention includes a light-source characterised in that the cooling-air channels are formed by sections of a continuous profiled material which is advantageous with regard to inexpensive production of the light-source.

The further development of the invention includes a light-source characterised in that the light-emitting diodes are arranged on a curved separation surface which is particularly well suited for treating workpieces or products on a curved section of the conveying path along which the workpieces or products are moved. Dished or domed light-sources of such a type are particularly suitable for use on cylinders by which printed products are conveyed.

By virtue of the arrangement of the light-emitting diodes on a concavely curved spherical surface, it is also possible for high illuminance values to be generated at the point of intersection of the axes of the various light-emitting diodes.

The further development of the invention includes a light-source characterised in that the light-emitting diodes exhibit a radiation pattern with an aperture angle from about 10° to about 60°, and preferably about 15° to 25°; which is advantageous with regard to having the intensity of illumination uniform in the treatment surface.

The further development of the invention includes a light-source characterised in that the light-emitting diodes are arranged on one or more printed circuit boards and the rear of these printed circuit boards is cooled by a cooling fluid. On the one hand a simple mounting of the LEDs is guaranteed; on the other hand, the LEDs that have been combined to form a unit can be cooled very effectively and intensely.

In this connection, a further development of the invention includes a light-source characterised in that the printed circuit board exhibits on the rear, preferably on both sides, a metal lamination conducting heat well, in particular a copper lamination, with the metal layer of the one side forming a plurality of conductive tracks to which the light-emitting diodes are connected, whereas the other metal layer is connected in heat-conducting manner to at least one cooling tube, in particular is soldered thereto. A good thermal contact between cooling tubes conducting cooling fluid and the LEDs is guaranteed in this very simple manner.

The further development of the invention includes a light-source characterised in that the printed circuit board carries a plurality of cooling tubes extending substantially parallel to one another which are connected at least one of their ends, preferably at both of their ends, by means of a head channel which provides an intense and identical cooling of the various LEDs which are supported by a printed circuit board.

The further development of the invention includes a light-source characterised in that the light-emitting diodes are provided on their mounting side with supply contacts and with at least one heat-dissipating contact and in that the heat-dissipating contacts of the light-emitting diodes are in heat-transmitting contact with a heat-dissipating surface of the housing which is also advantageous with regard to good dissipation of heat from the semiconductor materials of the light-emitting diodes.

The further development of the invention includes the arrangement of thermal contacts and power-supply contacts and a light-source characterised in that the power-supply contacts and the heat-dissipating contacts of the light-emitting diodes are arranged in separate regions of the mounting side of the light-emitting diodes, and the power-supply contacts and heat-dissipating contacts of the light-emitting diodes are each arranged in a common row or column and are orientated in alignment with one another, and the aligned heat-dissipating contacts are in communication with a heat-dissipating surface facing towards them which enables the dissipation of the heat and the supply of current to be effected by using busbars which run over and beyond a plurality of light-emitting diodes. In this way, a particularly clearly laid out and mechanically simple arrangement is obtained.

The further development of the invention includes a preferred interleaving of heat-conducting surfaces and power supply in a light-source characterised in that the power-supply contacts are connected to a connecting pcb which is arranged in each instance in a receiving groove in the housing, said receiving groove being situated between two adjacent heat-dissipating surfaces.

The further development of the invention includes a light-source characterised in that the bottom of the receiving grooves exhibits passageways for supply lines leading to the connecting pcbs where there is a large heat-dissipating metal volume in the vicinity of the individual light-emitting diodes, but nevertheless there is the possibility of a simple and direct supply of energy.

The further development of the invention includes a light-source characterised in that the heat-dissipating surface is formed on a housing which is traversed by coolant channels which is advantageous with regard to a good cooling of the heat-conducting surfaces, in turn, by means of coolant channels.

The further development of the invention includes a fluid cooling system for a light-source characterised in that at least some of the coolant channels conduct a liquid coolant, in particular water, which is particularly effective.

The further development of the invention includes a light-source characterised in that at least some of the coolant channels conduct a gaseous coolant, in particular air that serves likewise for the dissipation of heat from the environment of the light-emitting diodes, it being possible for the gaseous flow medium that has been heated up to be directed, on demand, towards the workpieces to be dried or towards the workpieces to be warmed up, so that this heat is rendered usable as process heat.

With the further development of the invention including a light-source characterised in that by using retaining plates the light-emitting diodes are pressed against the heat-dissipating surfaces which exhibit a window for each of the light-emitting diodes and a secure and precisely positioned fitting of the light-emitting diodes near the heat-conducting surfaces is obtained in simple manner.

The further development of the invention includes a light-source characterised in that the retaining frames each exhibit a fastening section which is free of windows and in which a fastening means is arranged which cooperates with a housing bearing the heat-dissipating surface which permits the retaining frames to be fixed tightly to a housing that bears the heat-conducting surfaces.

The further development of the invention includes a light-source characterised in that the retaining frames are arranged in rows or columns and are offset in relation to one another in the row-direction or column-direction in such a way that substantially the same number of light-emitting diodes is obtained overall in each column or row for the purpose of irradiating workpieces moved past it, or if such a light-source is moved in relation to a stationary workpiece, the various surfaces of the workpiece are irradiated with the same intensity of illumination. The drying or curing of the layers of material borne by the workpiece is consequently effected uniformly well.

The further development of the invention with a light-source characterised in that the fastening means cooperate with retaining means which each slightly overlap an adjacent retaining frame, the fastening means can at the same time fix the adjacent retaining frame securely. Each retaining frame is consequently firmly clamped at both ends, ensuring a secure and precise positioning of the retaining frames on the housing, and hence also of the light-emitting diodes above the contacts and heat-conducting surfaces cooperating with them.

The further development of the invention with a light-source characterised in that the marginal ends, in the line-direction or column-direction, of several adjacent frames of the peripheral retaining frames are fixed via a retaining strip to a housing bearing the heat-dissipating surface and the marginal retaining frames are fixed to the housing in particularly secure manner.

The further development of the invention includes a light-source characterised in that the windows exhibit window walls extending towards the outside of the retaining plate which is advantageous with regard to not occluding the marginal regions of the light bundle emitted by the light-emitting diodes.

The further development of the invention includes a light-source characterised in that the retaining frames are provided on two mutually opposing sides with complementary parts of a tongue-and-groove joint which is again advantageous with regard to good and secure positioning of the retaining frames on the housing of the light-source.

The further development of the invention includes a-light-source characterised in that the housing bearing the heat-dissipating surfaces is formed by a section of an extrusion profile which is manufactured from a material that conducts heat well, in particular aluminium, wherein the housing can be provided in cost-effective manner with a plurality of different channels which serve as coolant channels, diode-receiving grooves, mounting grooves, conduction channels. At the same time, a good dissipation of heat from the light-emitting diodes is guaranteed.

The further development of the invention includes a light-source characterised in that the extrusion profile is provided with at least one mounting groove which is advantageous with regard to a simple mounting of the light-source on a machine frame, with regard to a simple assembling of light-sources to form more extensive light-sources, and with regard to the fitting of auxiliary devices on the light-source.

The further development of the invention includes a light-source characterised in that the extrusion profile at least partially delimits an air channel integrally moulded right from the beginning, which does not have to be produced by machining.

Similarly, the further development of the invention with a light-source characterised in that the extrusion profile at least partially delimits a cable channel, provides a cable channel that is already entirely or largely prepared.

Light-emitting diodes typically have relatively small supply voltages (approximately in the region of 2.4 V). If light-emitting diodes of such a type are combined in groups of five or ten such as a light-source characterised in which groups of light-emitting diodes are electrically connected in series, supply voltages of 12 V or 24 V, respectively, or corresponding multiples of these values, are obtained, and inexpensive mains power packs for these supply voltages are available as standard components.

With the further development of the invention including a light-source characterised in that the power-supply contacts to be poled differently of adjacent light-emitting diodes are connected to one another via conductive tracks of a printed connecting pcb. The desired series connection of light-emitting diodes is obtained automatically upon bringing the light-emitting diodes arranged in matrix into contact with the connecting circuits situated underneath.

The further development of the invention includes a light-source characterised in that the power-supply contacts to be poled differently of adjacent light-emitting diodes are connected to one another via conductive tracks of a printed connecting pcb. This has the advantage that the failure of a single light-emitting diode results only in a slight change in the total quantity of light emitted in the light-source.

The further development of the invention includes a light-source characterised in that a connecting pcb supporting a group of light-emitting diodes carries two supply busbars parallel to one another, and the light-emitting diodes are rotated in such a way that the connecting lines of their anode contacts and cathode contacts extend at such an angle to the supply busbars that the anode contacts are situated above a first one of the supply busbars and the cathode contacts are situated above the second one of the supply busbars, and heat-dissipating contacts are situated to the side of the supply busbars, whereby the light-emitting diodes with respect to their vertical axis perpendicular to the mounting surface, it is ensured that current-supply surfaces and heat-dissipating surfaces situated alongside one another can be used even when the supply contacts and heat-dissipating contacts of the light-emitting diodes have the same distance from the vertical axis of the diodes.

BRIEF DESCRIPTION OF THE DRAWINGS

The invention will be elucidated in more detail below on the basis of exemplary embodiments with reference to the drawing. Shown in the latter are.

DETAILED DESCRIPTION OF THE PRESENT INVENTION

Figure 1:
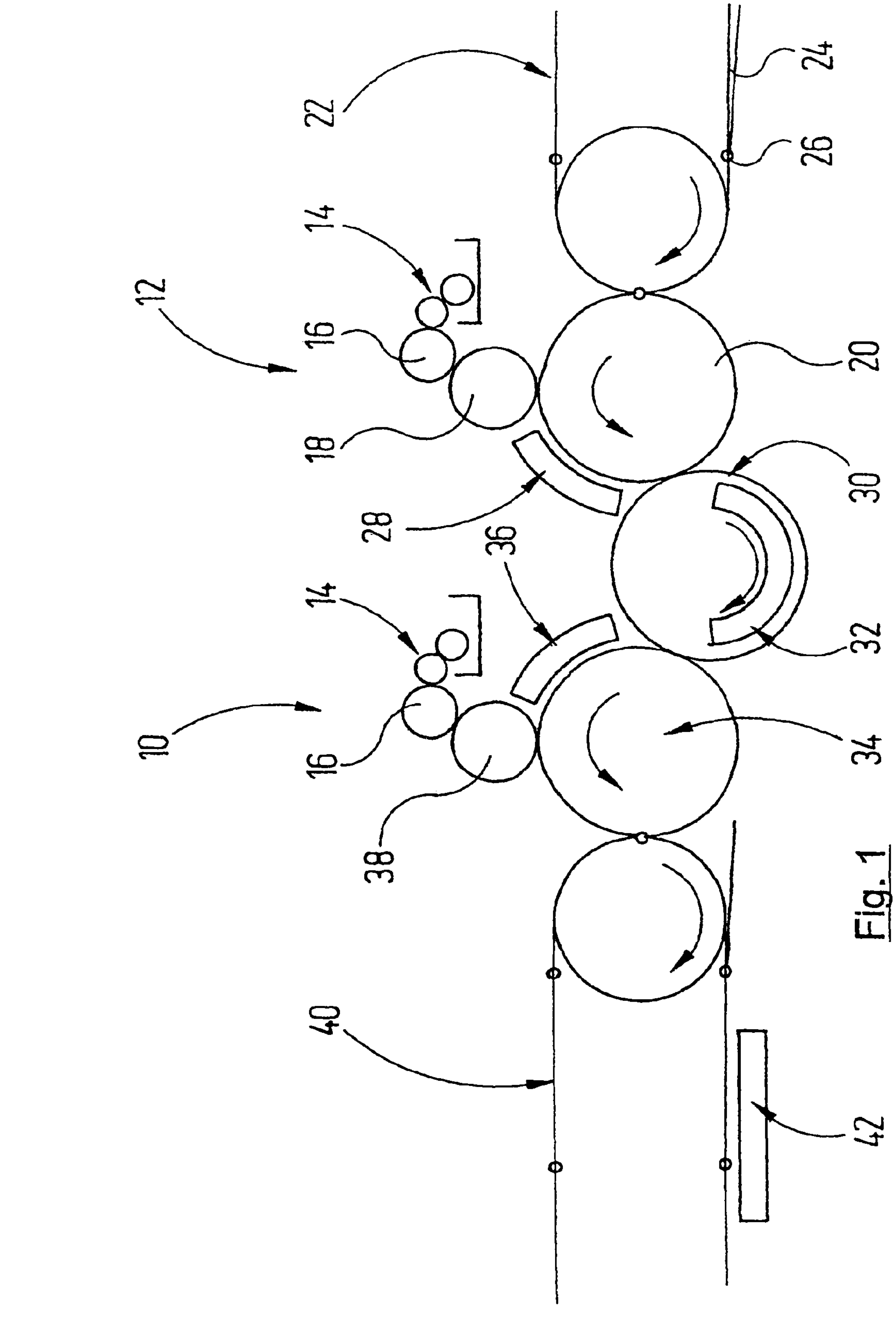
FIG. 1: a schematic detail from a printing press, in which various possibilities for UV drying of printed products running over cylinders and conveyed freely are shown.

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated.

In FIG. 1 a detail is reproduced from a sheet-fed printing press that includes two printing towers 10, 12. Each of the printing towers has an inking unit 14 which provides ink to an application cylinder 16. The latter supplies an impression cylinder 18 which cooperates with a counter-cylinder 20.

A conveyor 22, indicated schematically, carries individual printed sheets 24 to the counter-cylinder 20 using grippers 26. Said counter-cylinder accepts the printed sheets with its own grippers and carries them past the impression cylinder 18. By this means, a layer of printing-ink is produced on the printed sheet 24.

Upon further rotation of the counter-cylinder 20 the printed sheets run past a UV dryer, designated overall by 28, which is formed in partially cylindrical manner concentrically with the axis of the counter-cylinder 20.

Downstream of the UV dryer 28 the printed sheets 24 are then accepted by a transfer cylinder 30, the circumferential surface of which is transparent (cylinder made of quartz, glass or UV-transparent plastic or wire netting). In the interior of the transfer cylinder 30 there is arranged a UV dryer, designated overall by 32, which is formed in partially cylindrical manner concentrically with the axis of the transfer cylinder 30.

From the transfer cylinder 30 the printed sheets reach a further counter-cylinder 34 and, resting on the latter, are moved past in front of a further UV dryer 36 which again is formed in partially cylindrical manner concentrically with the axis of the counter-cylinder 34.

For the purposes of elucidation, let it be assumed that the counter-cylinder 34 cooperates with an impression cylinder 38 which applies a layer of clear lacquer onto the printing-ink.

From the impression cylinder 38 the printed sheets are accepted by a continuous conveyor 40.

In a horizontal section of the conveying path of the continuous conveyor 40 there is arranged a further UV dryer 42 which is flat.

FIG. 1 consequently shows various possibilities for the arrangement of UV dryers on curved and straight sections of the conveying path of printed sheets.

Figure 2:
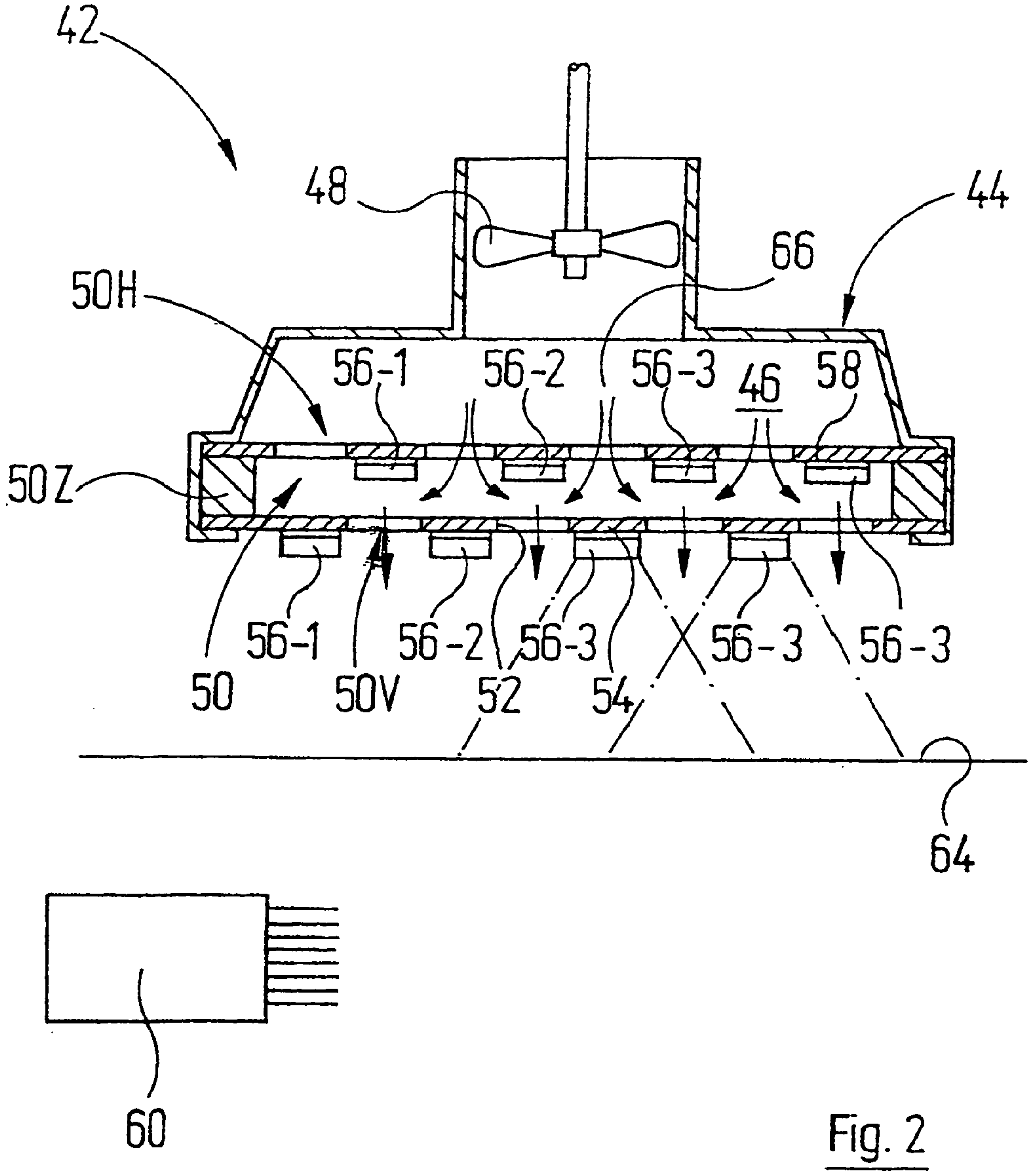
FIG. 2: a schematic representation of a flat UV dryer that is intended for drying printed products in a rectilinear section of their conveying path.

FIG. 2 shows particulars of the flat UV dryer 42. A housing 44 delimits a distribution chamber 46 which has air applied to it by means of a fan 48.

A front wall 50, designated overall by 50, of the housing 44 exhibits an anterior slotted plate 50V and a posterior slotted plate 50H, which are spaced by means of an intermediate frame 50Z.

The slotted plates 50V and 50H each have a plurality of slots 52, extending perpendicular to the plane of the drawing, and slats 54 remaining therebetween.

The slats 54 support rows of light-emitting diodes 56-1, 56-2 and 56-3.

The light-emitting diodes 56 emit in the ultraviolet, specifically at different wavelengths: the light-emitting diodes 56-1 have a wavelength of 256 nm; the light-emitting diodes 56-2 have a wavelength of 308 nm; and the light-emitting diodes 56-3 have a wavelength of 360 nm.

If desired, more than one row of a particular type of diode may also be provided on each of the slotted plates 50V and 50H, in order to have an increased power of a particular wavelength.

The rows of light-emitting diodes are capable of being switched on separately, in order to utilise individual wavelengths separately where appropriate. Furthermore, at least the light-emitting diodes situated in the end regions of the slats 54 are capable of being switched separately, in order to be able to take the width of the printed products into account.

Each row of light-emitting diodes is seated on an elongated printed circuit board 58 which carries the feed lines to the various light-emitting diodes. The printed circuit boards 58 are, in turn, connected to a mains power pack 60 which provides the operating voltages for the various light-emitting diodes.

As is evident from FIG. 2, the light-emitting diodes 56 each generate a UV light cone 62 with an aperture angle of about 60°. In this way, the various light cones of consecutive rows overlap in a plane 64 in which printed sheets to be dried are moved from right to left in the drawing.

It will be discerned that the printed sheets bearing a layer of printing-ink run successively in this way through UV-radiation regions of varying wavelength, so that varying chemical reactions in the printing-ink are triggered which bring about the curing and drying.

The light-emitting diodes 56 are cooled by means of the air curtains 66 which pass through between the slats 54. Heat absorbed by the air curtains 66 is conveyed to the upper sides of the printed sheets 24.

In FIG. 2 the spacing of the slotted plates 50V and 50H has been reproduced on an exaggeratedly large scale, in order to be able to show the flow conditions better. It is to be understood that, in practice, this spacing is chosen to be just so large that sufficient currents of cooling air are guaranteed.

A small spacing is desirable with regard to causing the entire light cone of the posterior light-emitting diodes to pass, as far as possible, directly through the slots 54 of the anterior slotted plates. But a silvering of the reverse side of the anterior slotted plate ultimately also provides for the utilisation of the beam-bundle portions that have not been let though directly from the reverse side of the slotted plate 50V.

Figure 3:
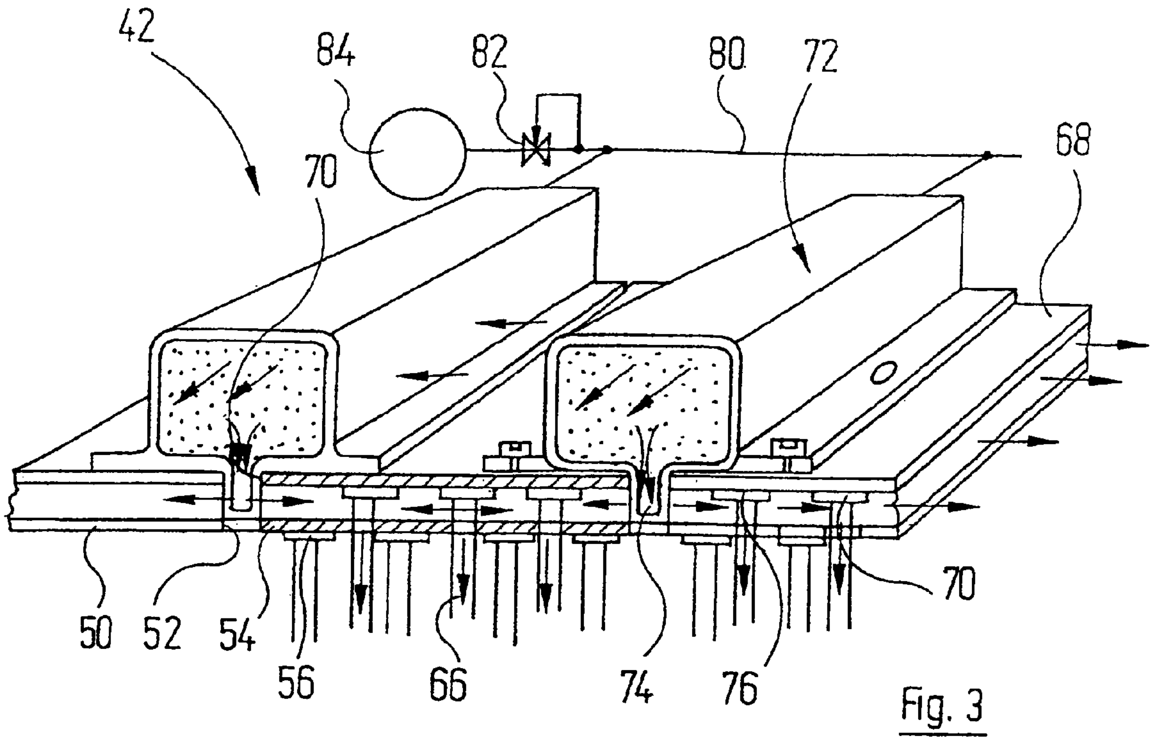
FIG. 3: an enlarged representation of a part of the UV dryer shown in FIG. 2, on the basis of which the cooling of the diodes of the dryer will be elucidated.

FIG. 3 shows particulars of the arrangement of UV light-emitting diodes in a modified UV dryer unit. Components that have already been elucidated above with reference to FIG. 2 are again provided with the same reference symbols and will not be described once more.

The cooling-air distribution chamber 46 is now delimited by the front wall 50, itself taking the form of a slotted plate, and a rear wall 68 which is arranged at a distance of a few mm above the front wall 50. The rear wall 68 has, in turn, transverse slots 70 at greater distances, which are in communication with the interior of cooling-air profiles 72 which is each provided, on the side adjacent to the rear wall 68, with an elongated outlet nozzle 74.

In order to have UV radiation also in the intermediate space between the light-emitting diodes supported by the front wall 50, light-emitting diodes 76 have been applied onto the rear wall 68, the axes of which are in alignment with the axes of the slots 52. The fitting of the light-emitting diodes 76 on the rear wall 68 is effected via printed circuit boards, not in any detail, which are comparable to the printed circuit boards 58.

The cooling-air profiles 72 are, in turn, in communication with a cooling-air line 80 which is in communication with a source 84 of cool compressed air via a pressure regulator 82.

It will be discerned that the dryer shown in FIG. 3 has very compact structure. By virtue of the fact that the rear wall 68 is convexly or concavely curved, the UV dryer can be curved in such a way that it is convexly or concavely partially cylindrical, as are the UV dryers 32, 36 and 42 shown in FIG. 1.

Figure 4:
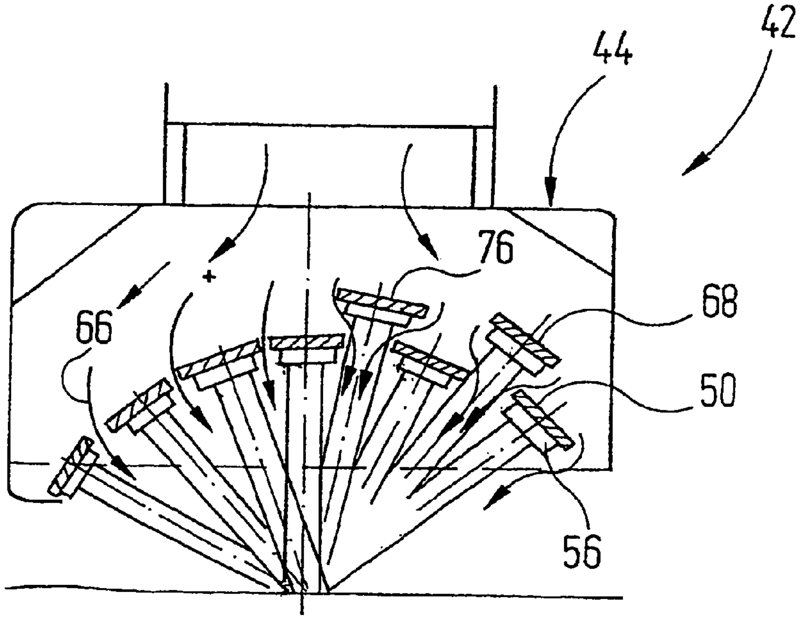
FIG. 4: a section through a modified UV dryer that is intended for drying printed products conveyed by means of a cylinder.

FIG. 4 shows a modified curved UV dryer of such a type, in which, however, a housing 44 is again provided, in a manner similar to that in the case of the dryer according to FIG. 2, whereas the front wall 50 is curved, as just described. Also with such a UV dryer, some of the light-emitting diodes that are shown at 76 can again be arranged in such a way that the light generated by them passes through the slots 52 in the front wall 50.

The arrangement according to FIG. 4 can be used for the purpose of directing the UV beam bundles jointly onto a treatment zone in which a high energy density is then available (as shown), or even for the purpose of subjecting a surface segment of a matching cylinder, the radius of which is only slightly smaller than that of the front wall 50, to UV light in substantially uniform manner.

Figure 5:
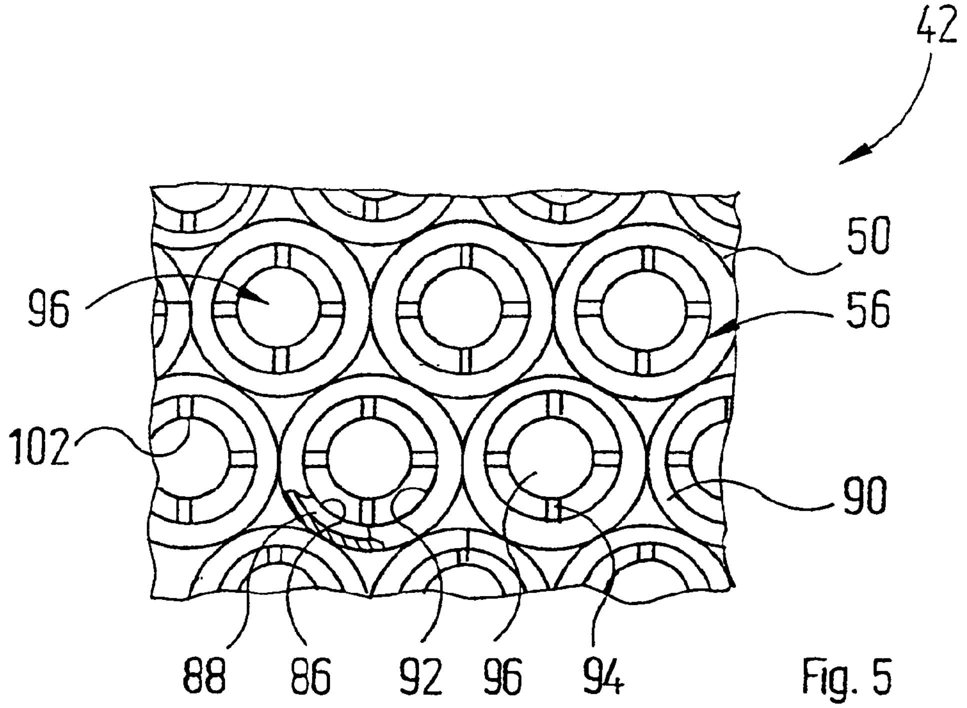
FIG. 5: a top view of a part of the diode array of a modified UV dryer.
Figure 6:
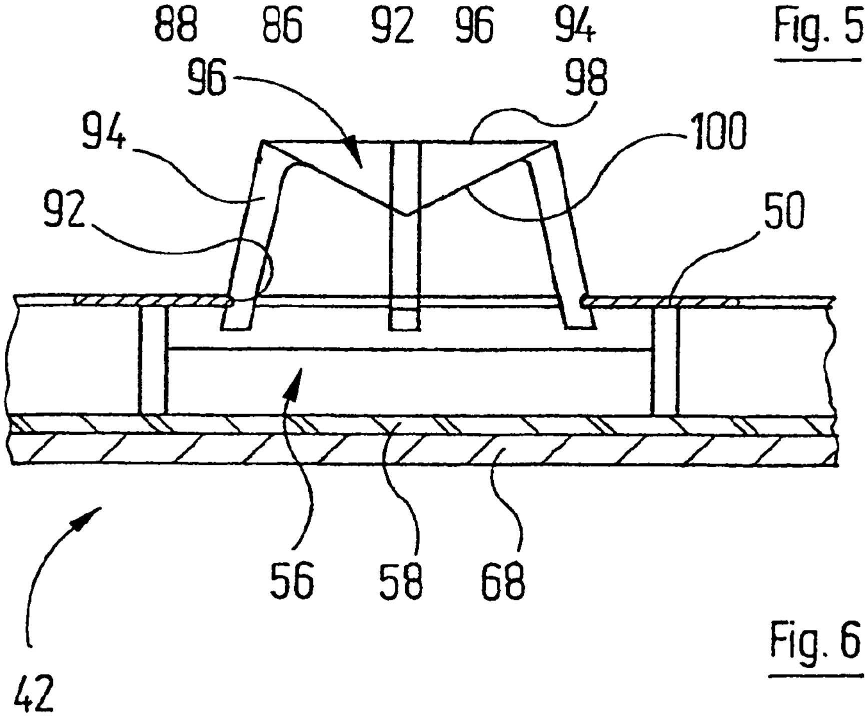
FIG. 6: an axial section through one of the diodes of the array according to FIG. 5, together with a region, surrounding said diode, of a mirror and also of a scattering element arranged upstream of a mirror aperture.

FIGS. 5 and 6 show a modified front wall 50 which supports light-emitting diodes 56. The light-emitting diodes 56 are circular discs and each have a window 86, from which UV radiation emerges, and a housing 88 which accepts the UV-emitting semiconductor material and, where appropriate, further electronic components, which are spatially closely adjacent to said material, and the connecting contacts of the light-emitting diode.

The front wall 50 has overall a specular—for example, smooth and chrome-plated-front side, and in the vicinity of the light-emitting diodes 56 a cup-shaped projection 90 is produced in each instance by deep drawing. The bottom of the projection 90 exhibits a window 92 which corresponds to the size of the window 86.

On the annular bottom wall of the projection 90, which is thus stationary, there are engaged four axial arms 94 which are equally distributed in the peripheral direction and which are moulded onto a scattering disc 96. The scattering disc 96 has a plane anterior end face 98 and a conical posterior end face 100. The aperture angle of the cone 100 in the exemplary embodiment that is represented is approximately 160°.

The scattering disc 96 is produced overall from in the UV-transmitting material (e.g. quartz), and the posterior end face 98 is vapour-coated so as to be semi-transmitting, specifically in such a manner that the transmissivity increases with increasing distance from the axis of the scattering disc.

In this way, the scattering disc 96 reflects a greater fraction from the central segment of the light bundle generated by the light-emitting diode 56 than from regions of the light bundle close to the edge. The decrease in the reflection factor in the radial direction is so chosen that it substantially compensates for the radial decrease in the radiation density in the light beam generated by the light-emitting diode 56. The reflected portions of the UV light reach the sections 102 of the specular front wall 50 situated radially outside the projection 90, which are concavely dished so greatly that the focal point of the corresponding small collecting mirrors is far removed from the conveying plane of the printed sheets.

In this way, the portions of the UV light reflected from the scattering discs 96 are likewise reflected in the direction of the treatment plane, so that the regions of the UV light source situated between the light-emitting diodes are not dark.

In the exemplary embodiments described above, the light-emitting diodes 56 of consecutive rows of the diode matrix are offset by half a separation in relation to one another. If, for example, a workpiece to be treated moves in the vertical direction in FIG. 5, the darker points of the radiation density correspond to a row of the brighter points of the radiation density of the following row, so that a uniform UV irradiation of the products moved past is obtained overall.

The front side of the silvered front wall 50 may (prior to the reflective coating) have been sandblasted or formed unevenly in some other way, in order to obtain a diffuse reflection thereon.

As is evident from FIG. 5, the light-emitting diodes are densely packed, practically without any spacing. The non-radiating surface regions are only small, so that a further array of light-emitting diodes provided in a posterior plane can be dispensed with, particularly if use is made of the homogenisation, described above, of the light flux by means of scattering discs.

Instead of individual scattering discs, use may also be made of a corresponding uninterrupted plane-parallel plate made of quartz or such like and exhibiting partial reflective coatings.

In the exemplary embodiments described above, the dissipation of waste heat from the light-emitting diodes 56 was effected by means of cooling air which is conducted past the light-emitting diodes.

Figure 7:
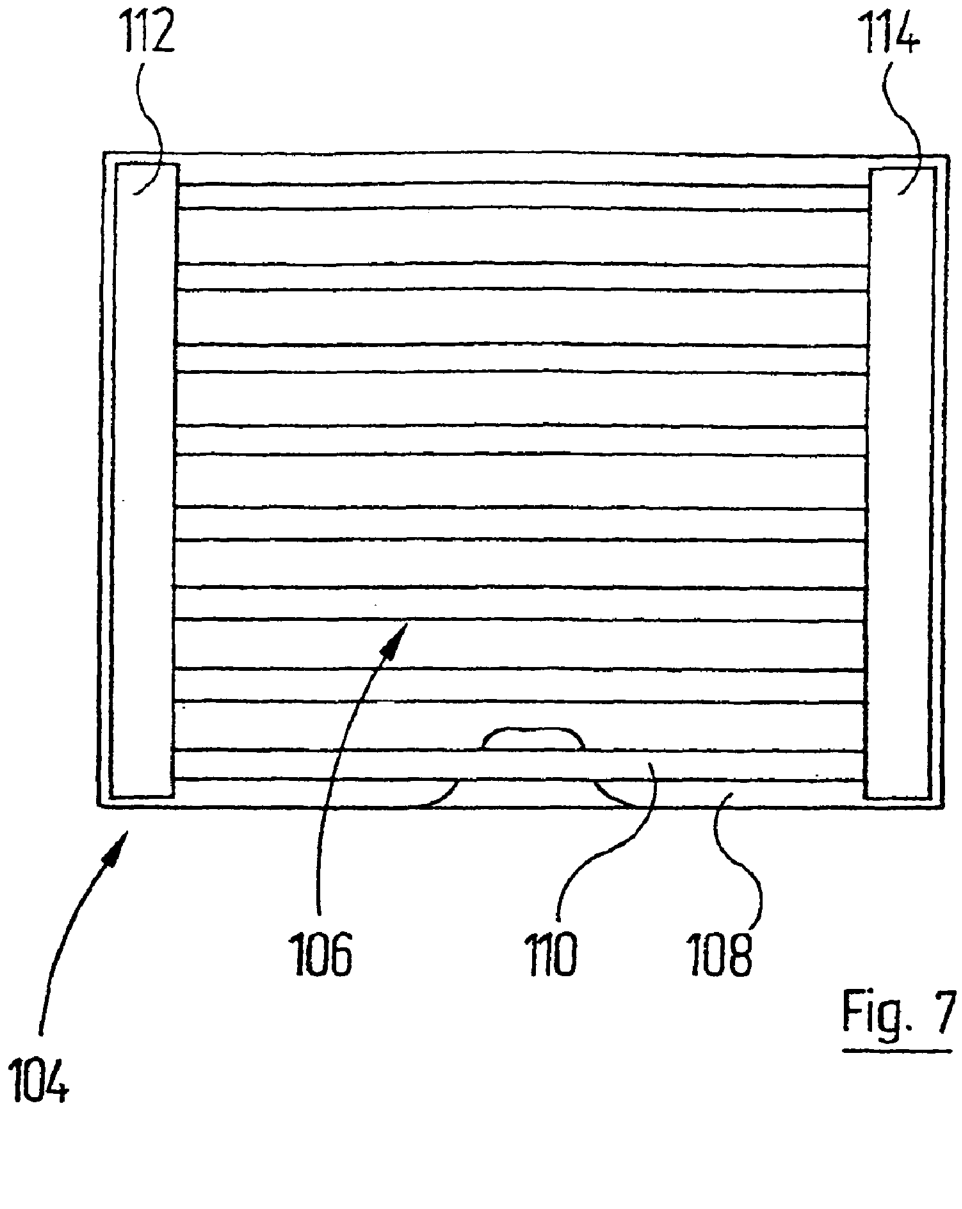
FIG. 7: a top view of the rear of a diode tile with fluid cooling.

FIG. 7 shows a diode tile, designated overall by 104, with integrated water cooling from the rear. The light-emitting diodes are located on the other side and have not been reproduced. By combining a plurality of diode tiles of such a type, flat or curved UV light sources having greater dimensions can be produced.

The diode tile 104 includes a printed circuit board 106 which is laminated with copper on both sides. On the lamination to be imagined below the plane of the drawing there are formed conductive tracks by which the various light-emitting diodes supported by this side of the printed circuit board using surface-mounted technology are connected to the mains power unit.

Rectilinear cooling tubes 110 made of copper are soldered in uninterrupted manner on the copper layer 108 of the printed circuit board 106 situated in the plane of the drawing. The two ends of the cooling tubes 110 are connected by means of head channels 112, 114 which are likewise soldered onto the copper layer 108 in uninterrupted manner. Of said head channels, under operational conditions one is connected to a source of cooling water, the other to a cooling-water drain.

With the aid of the water flowing through the cooling tubes 110 the copper layer 108 is cooled, and the cooling of the reverse sides of the light-emitting diodes 56 is effected from there.

In FIGS. 8 to 13 a tile-shaped light-source unit which exhibits a housing 122 is designated overall by 120.

In this connection it is a question of a length of an extruded aluminium profile which is formed on its upper side with a flat depression 124, from which three receiving grooves 126 spring back, the side walls of which each exhibits a shoulder 128.

Onto the shoulders 128, in the case of a fully assembled light-source unit 120, there are placed in each instance connecting pcbs 130 which will be described in greater detail later with reference to FIGS. 14 and 15 and which are indicated by broken lines in FIG. 12.

Figure 16:
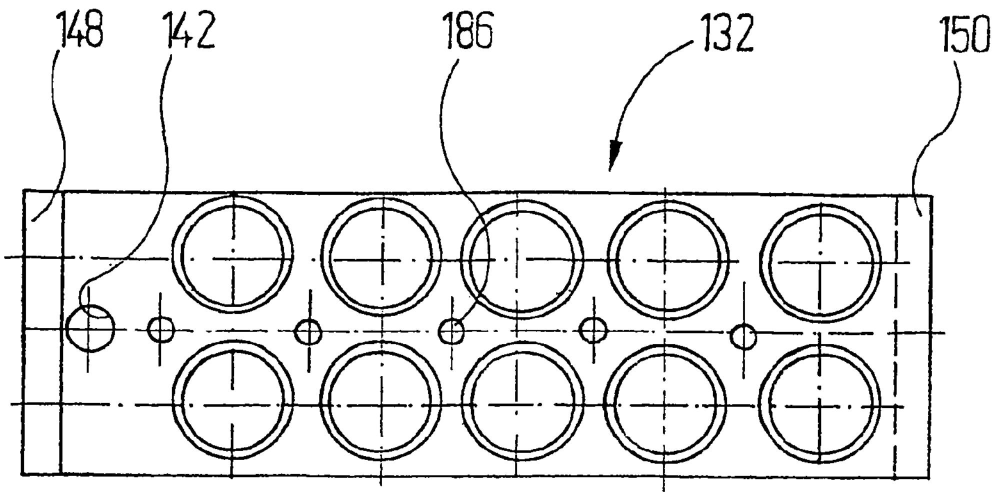
FIG. 16: a top view of a diode-retaining frame of the UV-light tiles according to FIGS. 8 to 13.
Figure 17:
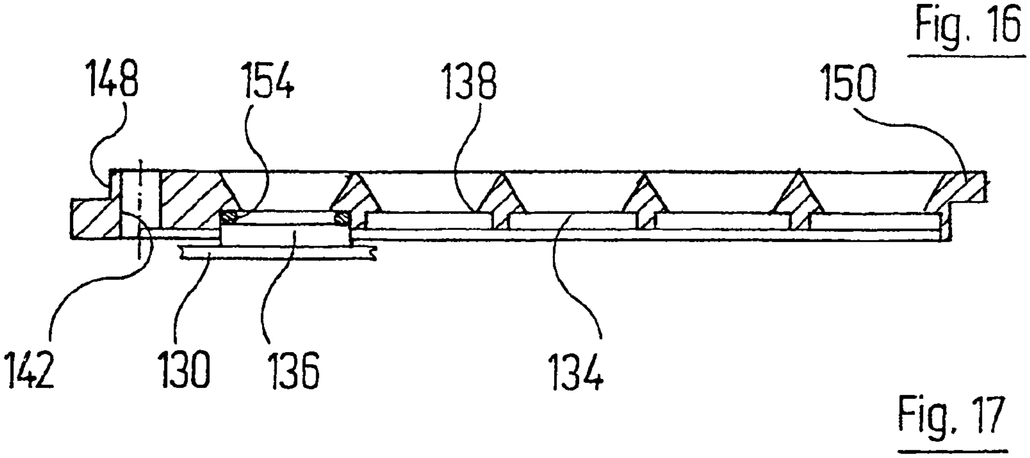
FIG. 17: a longitudinal section through the diode-retaining frame shown in FIG. 16.

Into the depression 124 there are screwed a plurality of retaining plates 132, designated overall by 132, which are reproduced in greater detail in FIGS. 16 and 17.

Each of the retaining plates 132 has circular depressions 134 on its underside, which each serve to receive the upper end of a circular-disc-shaped light-emitting diode 136 which emits in the UV region. On the upper side the retaining plate 132 is formed with windows 138, the walls of which are set at an angle of about 60° in relation to the plane of the plate.

Each of the retaining plates 132 has two rows of, in each instance, five windows 138 and, aligned herewith, depressions 134, and a plate section 140 situated on the right in the drawing in each instance, which is free of windows and exhibits a bore 142 for receiving a fastening screw 144.

Figure 8:
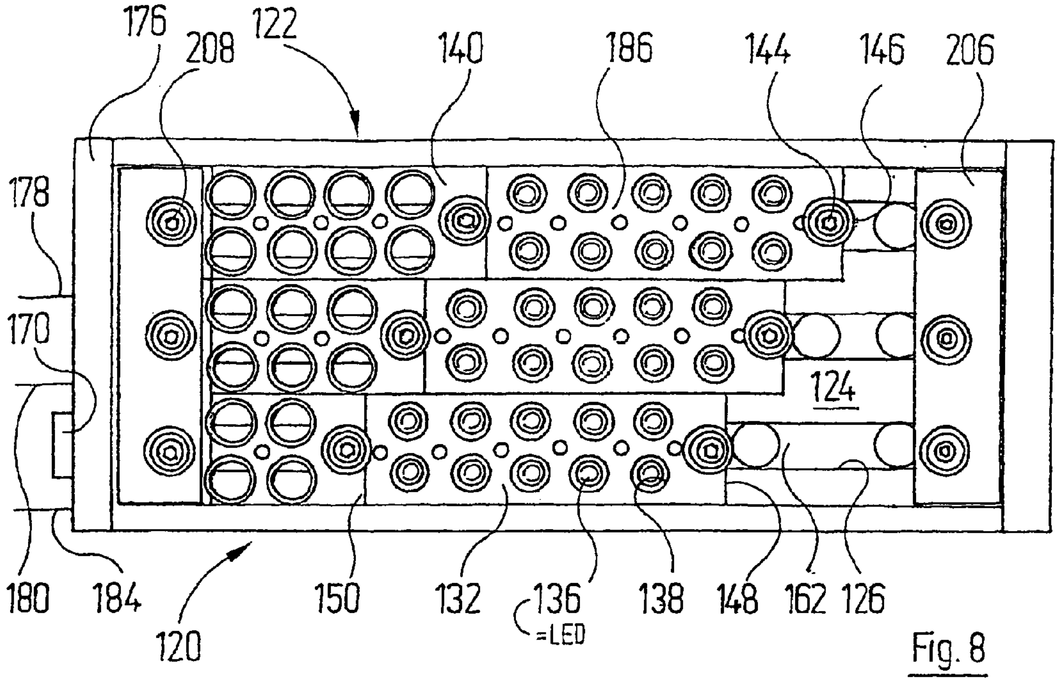
FIG. 8: a top view of a UV-light tile that has had components only partially inserted and that is part of a further modified UV dryer.
Figure 10:
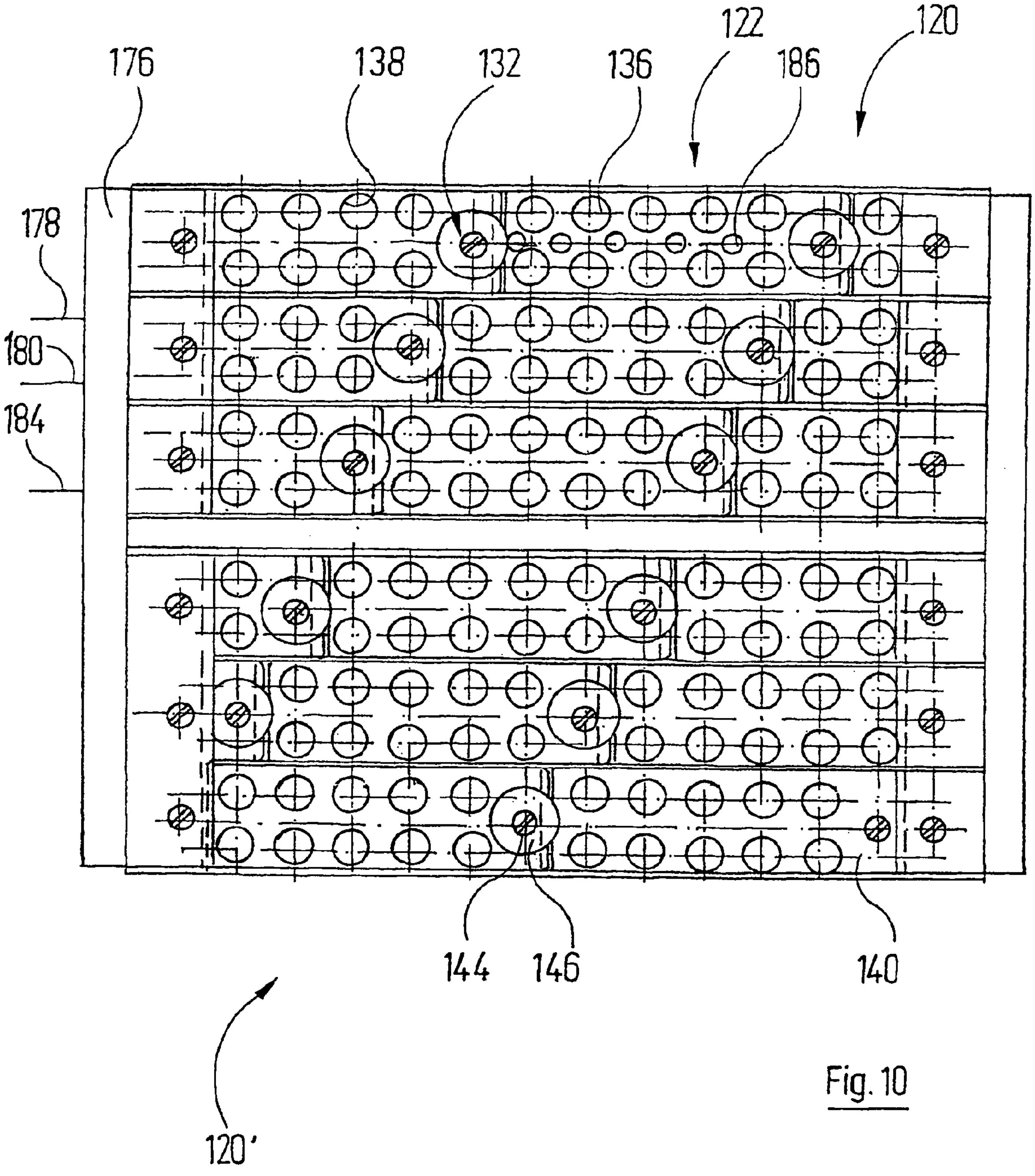
FIG. 10: a top view of two adjacent UV-light tiles with components fully inserted.
Figure 11:
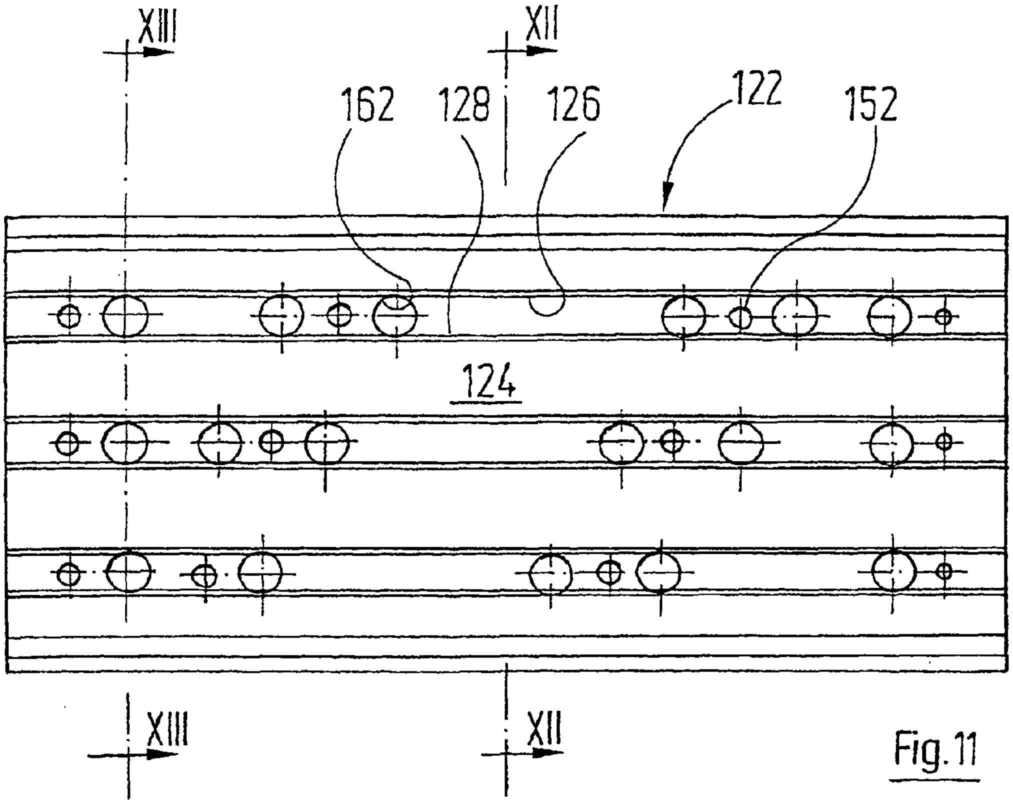
FIG. 11: a top view of the upper side of a light-tile housing without light-emitting diodes and diode-retaining plates.

The head of the fastening screw 144 cooperates with a circular retaining disc 146, the radius of which is such that it just slightly overlaps the adjacent edge of an adjacent retaining plate 132, as is evident from FIGS. 8 and 10.

In the section adjacent to the bore 142 the retaining plates 132 have a groove 148 in which a tongue 150 can be received in positive manner and which is supported by the other end of the adjacent retaining plate 132. In this way, a fastening screw 144 fixes the abutting adjacent ends of two adjacent retaining plates 132 on the bottom of the depression 124.

The height of the retaining plates 132 is chosen so as to correspond to the depth of the depression 124, so that the front side of the housing 122 and the front sides of the retaining plates 132 form an uninterrupted surface.

As is evident from FIGS. 8 and 10, the retaining plates 132 are each offset by one separation of the windows 138. Correspondingly, threaded bores 152 which are provided on the bottom of the depression 124 (see FIG. 11) are arranged correspondingly offset in relation to one another.

The retaining plates 132 adjacent to the edge of the light-source unit 120 are shortened so as to correspond to the offset of the retaining plates and include, in the case of the light-source unit shown in FIG. 8, four pairs of windows in the uppermost row on the left and one pair of windows on the right (plate not represented), three pairs of windows in the central row on the left and two pairs of windows on the right (plate not shown), and also two pairs of windows in the lowest row on the left and three pairs of windows on the right (plate not shown).

This is also clearly evident from the upper half of FIG. 10, where all the retaining plates 132 have been applied onto the depression 124.

In FIG. 10 another light-source unit 120' is furthermore represented which is mirror-inverted in relation to the light-source unit 120 (vertical plane of the mirror).

It will be discerned that a double light-source unit of such a type exhibits in all the vertical columns ten light-emitting diodes in each instance, so that, averaged over the columns of the light-source unit 120 and 120', in each instance there is the same total intensity of illumination. If workpieces to be irradiated are moved through below the double light-source unit of FIG. 10, said workpieces consequently receive the same quantity of UV light in all regions.

In order to press the light-emitting diodes 136 to the same extent in good contact against the connecting pcbs 130 independently of small manufacturing variations, at the depressions 134 an O-ring 154 may be provided in each instance, as indicated in FIG. 17, which presses the light-emitting diode 136 situated underneath elastically against the depression 124 or, to be more exact, against the connecting pcb 130.

The connecting pcbs 130 (see FIGS. 14 and 15) have contact-points 156A and 156K (or generally 156) which are soldered to the connecting contacts (anode and cathode) of the light-emitting diodes 136. Commercially available UV light-emitting diodes often have contacts already prepared with soldering tin, so that for the purpose of soldering the light-emitting diodes onto the connecting pcb 130 it suffices to attach the light-emitting diodes 136 onto the connecting pcbs 130 in the correct orientation and to heat the soldered points briefly, for example by means of hot air.

Figure 14:
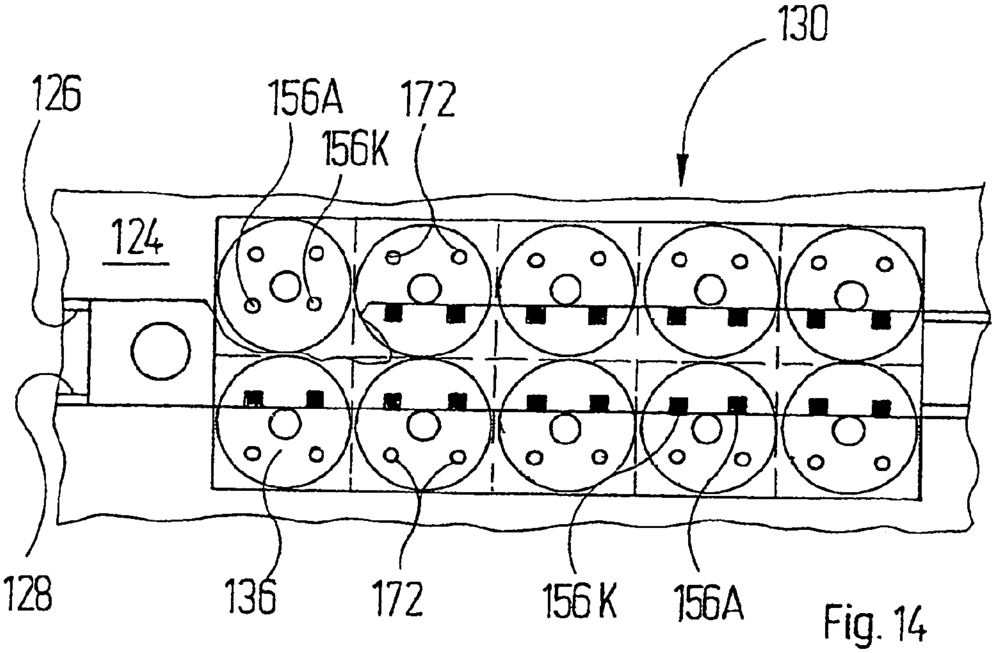
FIG. 14: a top view of the component-insertion side of a connecting pcb that is used in the UV-light tile according to FIGS. 8 to 13, the connecting contacts of various light-emitting diodes that are to be imagined above the connecting pcb having been drawn in broken lines.
Figure 15:
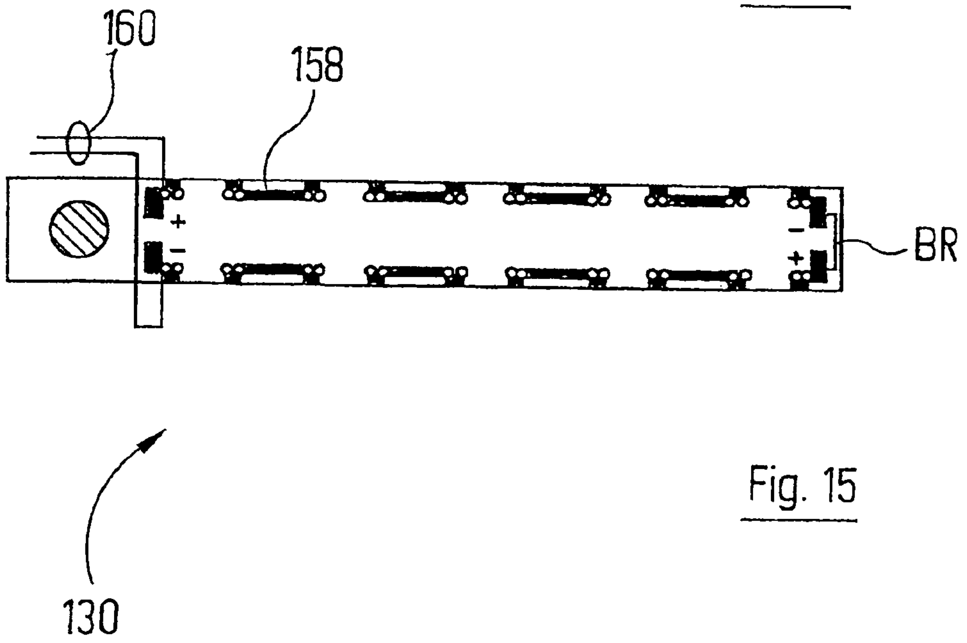
FIG. 15: a top view of the conductor side of the connecting pcb shown in FIG. 14.

With the connecting pcb shown in FIGS. 14 and 15 the cathode contacts 156K of the light-emitting diodes 136 are each connected to the anode contacts 156A of the adjacent light-emitting diodes by means of a conductive track 158. The five light-emitting diodes of a row are consequently connected in series. Given a typical operating voltage for a light-emitting diode of 2.4 V, an operating voltage of 12 V is consequently obtained for five light-emitting diodes situated alongside one another and connected in series.

If the conductive tracks situated on the right in the drawing are connected to one another by means of a bridge, the upper group of five light-emitting diodes can again be connected in series to the lower group of five light-emitting diodes, and a total supply voltage for the two-times-five light-emitting diodes is obtained at a level of 24 V. However, both groups may also be left separate, so that there is an operating voltage of 12 V for the connecting pcb 130. At the designated points a positive supply conductor and a negative supply conductor can then be soldered onto said connecting pcb.

Figure 13:
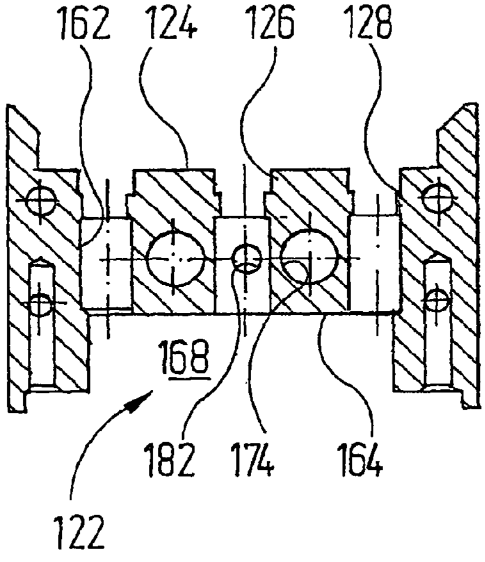
FIG. 13: a transverse section through the housing shown in FIG. 11 along section line XIII-XIII therein.

These supply conductors for a connecting pcb 130 extend through aligned vertical bores 162 which penetrate the housing 122 in the vertical direction, as is well evident from FIG. 13 in particular.

Figure 9:
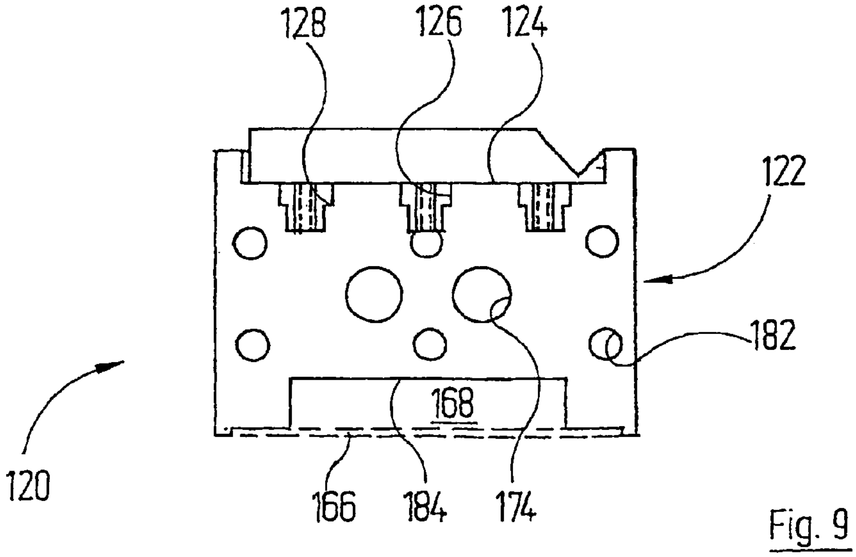
FIG. 9: a top view of the end face of the UV-light tile shown in FIG. 8.

In the underside of the housing 122 a depression 164 extending in the longitudinal direction is provided which together with a cover plate 166 indicated by broken lines in FIG. 9, which seals the underside of the housing 122, predetermines a cable channel 168. In the latter the various supply lines 160 extend as far as the end face of the light-source unit 120 or 120, where they are connected to a connecting plug which is indicated in FIG. 8 by broken lines at 170.

Figure 12:
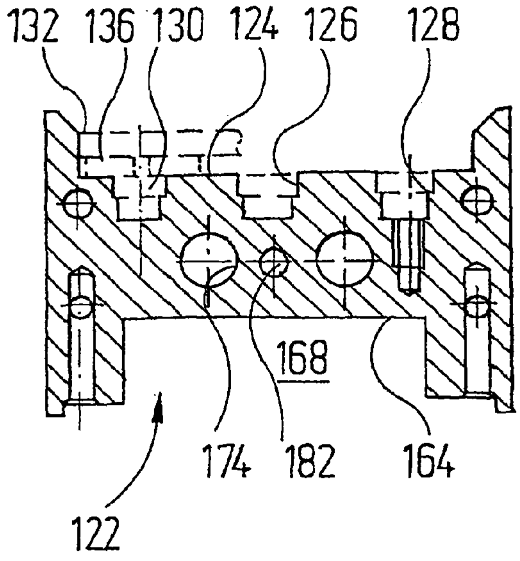
FIG. 12: a transverse section through the housing shown in FIG. 11 along section line XII-XII therein.

As is evident from FIGS. 12 and 13, the location of the shoulders 128 is so chosen that the upper side of the connecting pcbs 130 is in alignment with the bottom of the depression 124. Hence heat-dissipating contacts 172 of the various light-emitting diodes 136 are necessarily in heat-conducting contact with the upper side of the bottom of the depression 124. In this way, the heat arising in the light-emitting diodes 136 in the course of operation is dissipated well to the housing 122, which consists of material that conducts heat well, such as aluminium.

The upper side of the bottom of the depression 124 is therefore also designated as a heat-dissipating surface.

Coolant channels 174 are incorporated into the housing 122 during injection moulding, said coolant channels being connected, via end parts 176 attached onto the end faces of the housing 122, to a feed line 178 or to a return line 180 for cooling water or to one another. In this way, the heat generated by the light-emitting diodes 136 is dissipated very effectively overall, in which connection the housing 122 may have compact dimensions.

In the housing 122 there are provided moreover further coolant channels 182 extending in the longitudinal direction, which are connected to a compressed-air line 184 via the end parts 176. Via vertical branch channels 186 the coolant channels 182 are in communication with the front side of the retaining plates 132. Air emerging there has absorbed heat in the course of flowing through the housing 122, and is able to carry this heat in the form of process heat to the workpiece to be treated. Via the quantity of the water that is moved via the coolant channels 174 it is possible to adjust how hot the air is that is emitted via the branch channels 186.

As is evident from FIG. 12, the width of the receiving grooves 126 is precisely such that they are able to receive the connecting pcbs 130. The width of said connecting pcbs is such that conductive tracks which extend in the longitudinal direction and which electrically connect in series the consecutive light-emitting diodes 136 in a row can be accommodated on the connecting pcb 130.

From FIG. 14 it is well evident that the heat-dissipating contacts 172 come to be situated outside the connecting pcb 130 and are consequently situated on the bottom of the depression 124 when the light-source unit has been assembled in the operational state.

Figure 18:
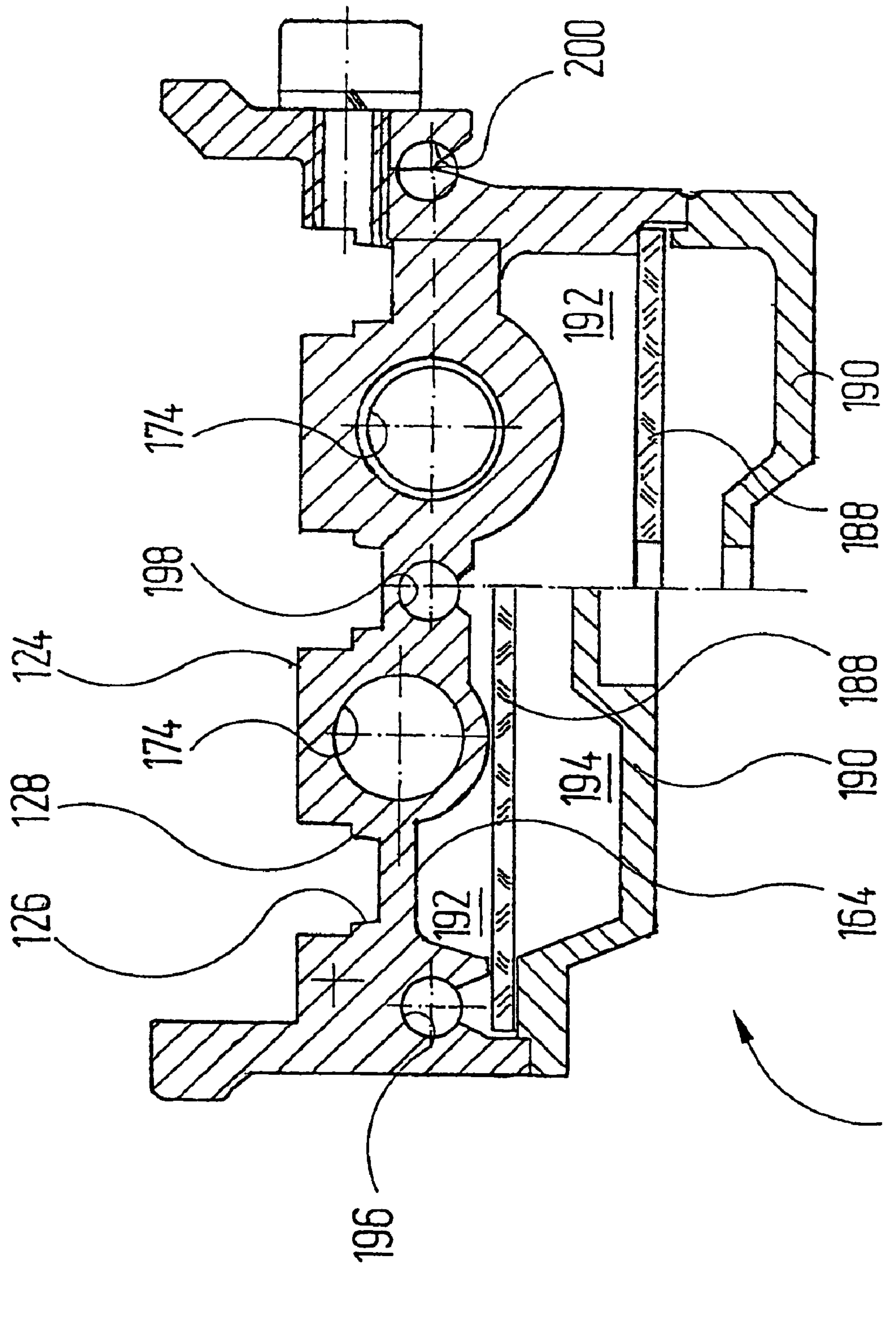
FIG. 18: a transverse section through a modified housing for a UV-light tile, wherein two alternative exemplary embodiments are shown, to the right and to the left of the centre line.

FIG. 18 shows, on the left and on the right of the centre line, two alternatives for a modified housing 122, the underside of which can be subdivided, by using a partition 188 and a cover plate 190, into two channels 192, 194 which extend in the longitudinal direction and which can be used as an air channel or as a cable channel. In this housing 122 only the coolant channels 174 supplied with fluid are present; further open channels 196, 198, 200 serve as receptacles for self-tapping screws with which end parts of the housing can be fitted to said housing.

Figure 19:
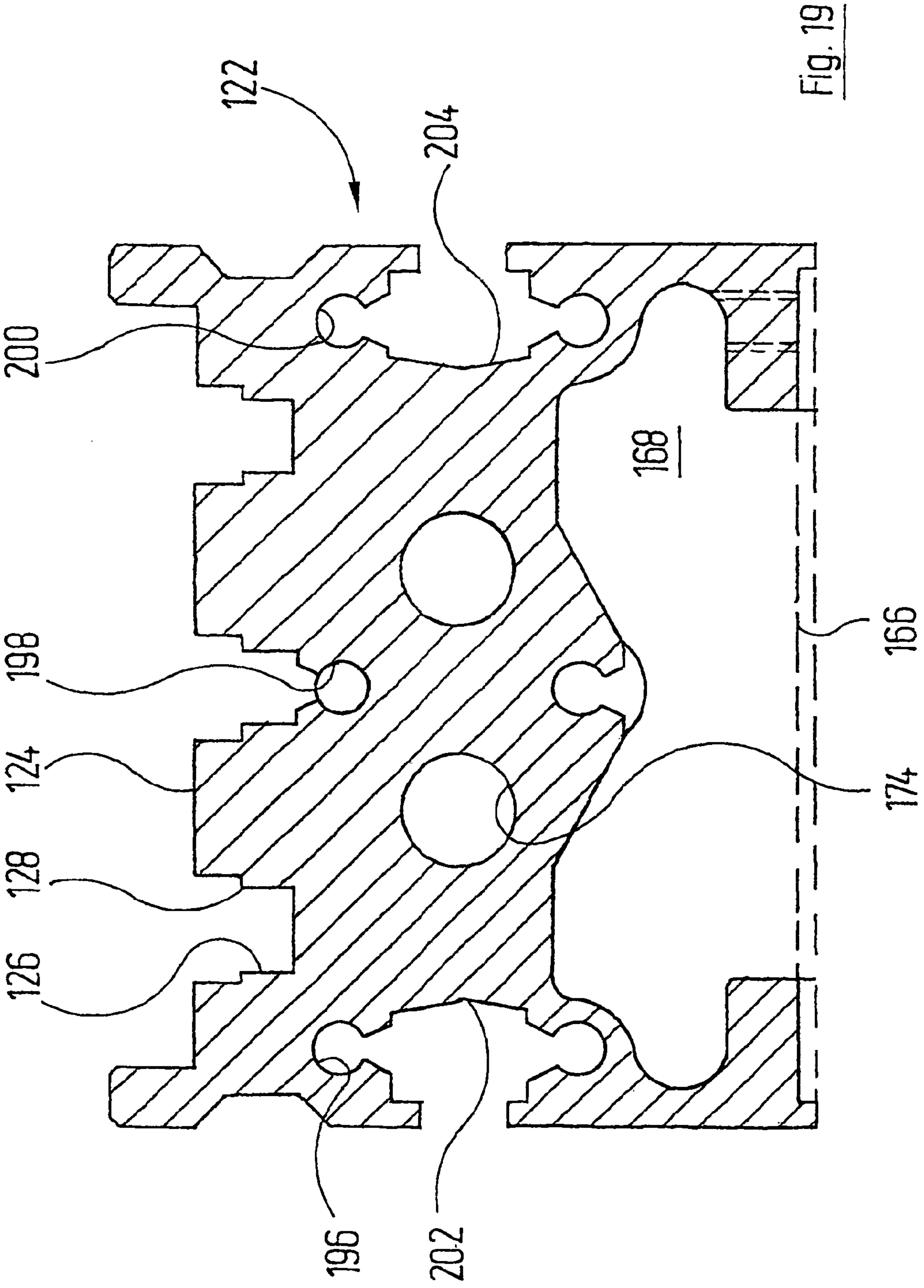
FIG. 19: a transverse section through another modified housing for a UV-light tile.

The further modified housing shown in FIG. 19 resembles that according to FIG. 18, but mounting grooves 202, 204 are also provided at the sides, which are able to receive base sections of attachments or housing-coupling elements to be fitted to the light-source unit.

Figures 20, 21:
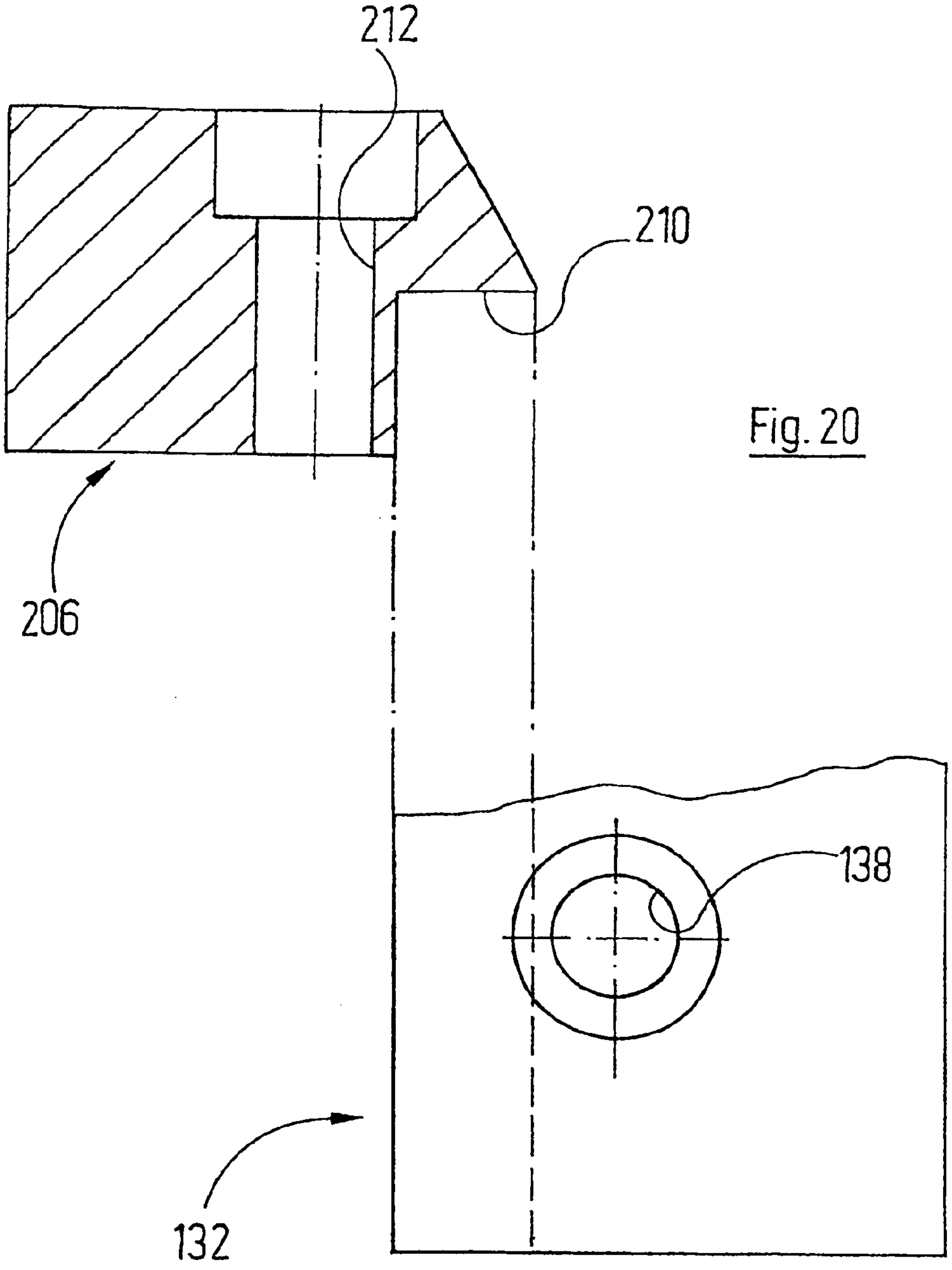
FIG. 20: an enlarged transverse section through a retaining strip with which diode-retaining frames are firmly clamped to the light-source housing.
FIG. 21: an enlarged top view of an end section of a diode-retaining frame.

FIG. 20 shows, on an enlarged scale, a transverse section through one of the two retaining strips 206 which overlaps the marginal ends of the retaining plates 132 and presses against the is depression 124 under the force of fastening screws 208.

In FIG. 21 the edge section of a retaining plate 132 has been rotated out of its plane by 90° but has been represented in the longitudinal relative position, with respect to the retaining strip 206, that it occupies in the mounted light-source unit 120. It will be discerned that the edge of this retaining plate 132 fits exactly into a lower recess 210 in the retaining strip 206.

Furthermore, the retaining strip 206 is provided with a stepped bore 212 for receiving a fastening screw 208 (see FIG. 1).

In the exemplary embodiments according to FIGS. 8 to 21 the front sides of the retaining plates 132 are buffed and chrome-plated, so that they again form a reflecting surface.

Figure 22:
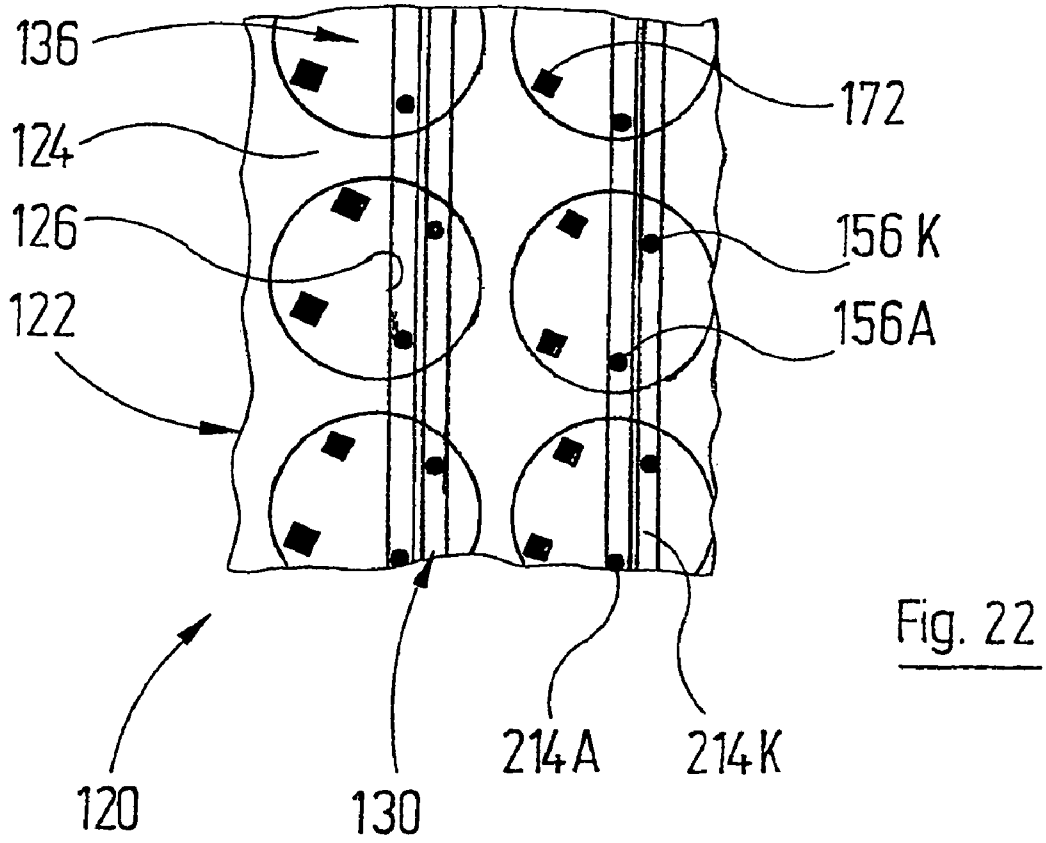
FIG. 22: a schematic partial top view of a UV-light tile in which the light-emitting diodes are operated in parallel.

FIG. 22 shows a top view of a part of a UV-light tile 120 without the retaining plates 132. Components already elucidated with reference to other exemplary embodiments are again provided with the same reference symbols, even if they differ in particulars, and will not be described in detail once more.

Light-emitting diodes 132 have been represented as if they were transparent, in order to be able to show the anode-connecting contacts 156A and cathode-connecting contacts 156K, as well as an anode-supply busbar 214A and a cathode-supply busbar 214K at the same time.

The supply contacts 156 (round dots) of a light-emitting diode 132 and the heat-dissipating contacts 172 thereof (small squares) have the same spacing from the axis of the circular disc (vertical axis of the light-emitting diode) and are situated at the corners of a square. In order nevertheless to guarantee that working is able to proceed with parallel supply busbars 214, and that the dissipation of heat to the bottom of the depression 124 (heat-dissipating surface) can take place, the edge of the square that is predetermined by the connecting line of the supply contacts 156A and 156K has been tilted by about 20 degrees towards the direction of the supply busbars 214. This is achieved by means of an appropriate twisting of the light-emitting diodes about their vertical axis.

By virtue of the high packing of light-emitting diodes, the exemplary embodiments, described above, of flat UV light sources result in a radiation density that is sufficient for curing UV printing-inks. By superimposition of the light bundles in the case of convex curvature of the wall supporting the light-emitting diodes, as shown in FIG. 4, the radiation density in the treatment surface can be increased further.

The flat UV light sources described above are distinguished by very simple mechanical structure. They are also low-maintenance in long-term operation, since the light-emitting diodes have a long service life in comparison with conventional UV light sources. The mains power pack for the operation of such UV light sources can be of very compact and simple construction.

The UV light source itself is also compact and can be adapted in simple manner to varying geometries of the conveying path of the products to be treated.

Flat UV light sources have been described above in connection with the drying of printing-inks on sheet-like printed products. It will be understood that they can also be employed for other irradiation purposes that require planar or focused UV light. These purposes include, in particular, the curing or drying of plastic moulding compounds in connection with the imprinting or coating of products made of sheet metal, foils, wood, glass and plastics, such as plastic containers and printed circuit boards. The UV light sources according to the invention can also be employed with advantage for planar intensive disinfection, for the initiation of chemical reactions, and for biochemical reactions.

It is again emphasized that the above-described embodiments of the present invention, particularly, any "preferred" embodiments, are possible examples of implementations merely set forth for a clear understanding of the principles of the invention. Many variations and modifications may be made to the above-described embodiments of the invention without substantially departing from the spirit and principles of the invention. All such modifications are intended to be included herein within the spirit of the invention and the scope of protection is only limited by the accompanying claims.

The invention claimed is:

1. A UV light source comprising: a plurality of UV light-emitting diodes supported by a wall and arranged in a matrix, wherein the wall includes cooling air apertures that are in communication with a source of cooling air and are situated in the vicinity of the light emitting diodes.

2. The light source of claim 1, wherein the cooling-air apertures are in communication with a distribution chamber which is delimited by a rear wall and by a front wall supporting the light-emitting diodes.

3. The light source of claim 2, wherein the front wall exhibits cooling-air slots extending parallel to one another, the width of which is comparable to the dimension of a light-emitting diode, and in that further light-emitting diodes which are in alignment with the cooling-air slots are provided downstream of the front wall.

4. The light source of claim 2, wherein the distribution chamber have cooling air applied to it via supply slots which are in communication with cooling-air channels.

5. The light source of claim 4, wherein the cooling-air channels re formed by sections of a continuous profiled material.

6. The light source of claim 1, wherein the light-emitting diodes are arranged in densely packed manner.

7. The light source of claim 1, wherein the light-emitting diodes are each arranged downstream of an aperture in a mirror.

8. The light source of claim 7, wherein the mirror exhibits scattering surface irregularities.

9. The light source of claim 7, wherein the mirror exhibits dished or domed surface sections.

10. The light source of claim 9, wherein surface sections situated between the apertures in the mirror are convexly curved.

11. The light source according of claim 9, wherein surface sections of the mirror surrounding the apertures are concavely curved.

12. The light source of claim 1, further comprising a scattering unit arranged upstream of the light-emitting diodes.

13. The light source of claim 7, further comprising a scattering unit arranged upstream of the light-emitting diodes wherein the scattering unit exhibits scattering elements situated upstream of the apertures in the mirror.

14. The light source of claim 13, wherein the scattering element exhibits diminishing scattering power with increasing spacing from the axis of the assigned light-emitting diode.

15. The light source of claim 1, wherein the light-emitting diodes include light-emitting diodes with varying operating wavelength.

16. The light source of claim 1, wherein the light-emitting diodes are arranged in consecutive rows.

17. The light source of claim 16, wherein the light-emitting diodes of consecutive rows are offset in relation to one another.

18. The light source of claim 1, wherein the light-emitting diodes are arranged on a curved separation surface.

19. The light source of claim 1, wherein the light-emitting diodes exhibit a radiation pattern with an aperture angle from about 10° to about 60°.

20. The light source of claim 1, wherein the light-emitting diodes are arranged on one or more printed circuit boards and the rear of these printed circuit boards is cooled by a cooling fluid.

21. The light source of claim 20, wherein the printed circuit board exhibits on the rear, a metal lamination conducting heat well, with the metal layer forming a plurality of conductive tracks to which the light-emitting diodes are connected, whereas the other metal layer is connected in heat-conducting manner to at least one cooling tube.

22. The light source of claim 21, wherein the printed circuit board carries a plurality of cooling tubes extending substantially parallel to one another which are connected at least one of their ends, by means of a head channel.

23. The light source of claim 1, wherein groups of light emitting diodes are electrically connected in series.

24. The light source of claim 23, wherein the power supply contacts to be poled differently of adjacent light-emitting diodes are connected to one another via conductive tracks of a printed connecting pcb.

25. The light source of claim 1, wherein at least some of the light-emitting diodes are electrically connected in parallel.

26. The light source of claim 25, further comprising a connecting pcb supporting a group of light-emitting diodes and carrying carries two supply busbars parallel to one another, and the light-emitting diodes are rotated in such a way that the connecting lines of their anode contacts and cathode contacts extend at such an angle to the supply busbars that the anode contacts are situated above a first one of the supply busbars and the cathode contacts are situated above the second one of the supply busbars, and heat-dissipating contacts are situated to the side of the supply busbars.

27. A UV light source comprising:

a housing; and, a plurality of light-emitting diodes arranged in a matrix and supported by a supporting structure, wherein the light-emitting diodes are provided on their mounting side with power supply contacts and with at least one heat-dissipating contact that is in heat-transmitting contact with a heat-dissipating surface of the housing.

28. The light source of claim 27, wherein the light-emitting diodes are arranged in densely packed manner.

29. The light source of claim 27, wherein the light-emitting diodes are each arranged downstream of an aperture in a mirror.

30. The light source of claim 29, wherein the mirror exhibits scattering surface irregularities.

31. The light source of claim 29, wherein the mirror exhibits dished or domed surface sections.

32. The light source of claim 31, wherein surface sections situated between the apertures in the mirror are convexly curved.

33. The light source according of claim 31, wherein surface sections of the mirror surrounding the apertures are concavely curved.

34. The light source of claim 27, further comprising a scattering unit arranged upstream of the light-emitting diodes.

35. The light source of claim 29, further comprising a scattering unit arranged upstream of the light-emitting diodes wherein the scattering unit exhibits scattering elements situated upstream of the apertures in the mirror.

36. The light source of claim 35, wherein the scattering element exhibits diminishing scattering power with increasing spacing from the axis of the assigned light-emitting diode.

37. The light source of claim 27, wherein the light-emitting diodes include light-emitting diodes with varying operating wavelength.

38. The light source of claim 27, wherein the light-emitting diodes are arranged in consecutive rows.

39. The light source of claim 38, wherein the light emitting diodes of consecutive rows are offset in relation to one another.

40. The light source of claim 27, wherein the light-emitting diodes are arranged on a curved separation surface.

41. The light source of claim 27, wherein the light-emitting diodes exhibit a radiation pattern with an aperture angle from about 10° to about 60°.

42. The light source of claim 27, wherein the light emitting diodes are arranged on one or more printed circuit boards and the rear of these printed circuit boards is cooled by a cooling fluid.

43. The light source of claim 42, wherein the printed circuit board exhibits on the rear, a metal lamination conducting heat well, with the metal layer forming a plurality of conductive tracks to which the light-emitting diodes are connected, whereas the other metal layer is connected in heat-conducting manner to at least one cooling tube.

44. The light source of claim 43, wherein the printed circuit board carries a plurality of cooling tubes extending substantially parallel to one another which are connected at least one of their ends, by means of a head channel.

45. The light source of claim 27, wherein the power supply contacts and the heat-dissipating contacts of the light-emitting diodes are arranged in separate regions of the mounting side of the light-emitting diodes, and the power-supply contacts and heat-dissipating contacts of the light-emitting diodes are each arranged in a common row or column and are orientated in alignment with one another, and the aligned heat-dissipating contacts are in communication with a heat dissipating surface facing towards them.

46. The light source of claim 45, wherein the power supply contacts are connected to a connecting pcb which is arranged in each instance in a receiving groove in the housing, said receiving groove being situated between two adjacent heat-dissipating surfaces.

47. The light source of claim 46, wherein the bottom of the receiving grooves exhibits passageways for supply lines leading to the connecting pcb.

48. The light source of claim 27, wherein the heat dissipating surface is formed on a housing which is traversed by coolant channels.

49. The light source of claim 48, wherein at least some of the coolant channels conduct a liquid coolant, in particular water.

50. The light source of claim 48, wherein at least some of the coolant channels conduct a gaseous coolant, in particular air.

51. The light source of claim 27, further comprising retaining plates wherein by the use thereof, the light-emitting diodes are pressed against the heat-dissipating surfaces which exhibit a window for each of the light emitting diodes.

52. The light source of claim 51, wherein the retaining frames each exhibit a fastening section which is free of windows and in which a fastening means is arranged which cooperates with a housing bearing the heat dissipating surface.

53. The light source of claim 52, wherein the retaining frames are arranged in rows or columns and are offset in relation to one another in the row-direction or column-direction in such a way that substantially the same number of light-emitting diodes is obtained overall in each column or row.

54. The light source of claim 52, wherein the fastening means cooperates with retaining means, which each slightly overlap an adjacent retaining frame.

55. The light source of claim 51, wherein the marginal ends, in the line-direction or column-direction, of several adjacent frames of the peripheral retaining frames are fixed via a retaining strip to a housing bearing the heat dissipating surface.

56. The light source of claim 51, wherein the windows exhibit window walls extending towards the outside of the retaining plate.

57. The light source of claim 51, wherein the retaining frames are provided on two mutually opposing sides with complementary parts of a tongue-and-groove joint.

58. The light source of claim 51, wherein the housing bearing the heat-dissipating surfaces is formed by a section of an extrusion profile which is manufactured from a material that conducts heat well.

59. The light source of claim 58, wherein the extrusion profile is provided with at least one mounting groove.

60. The light source of claim 58, wherein the extrusion profile at least partially delimits an air channel.

61. The light source of claim 58, wherein the extrusion profile at least partially delimits a cable channel.

62. The light source of claim 27, wherein groups of light emitting diodes are electrically connected in series.

63. The light source of claim 61, wherein the power supply contacts to be poled differently of adjacent light-emitting diodes are connected to one another via conductive tracks of a printed connecting pcb.

64. The light source of claim 27, wherein at least some of the light-emitting diodes are electrically connected in parallel.

65. The light source of claim 64, further comprising a connecting pcb supporting a group of light-emitting diodes and carrying carries two supply busbars parallel to one another, and the light-emitting diodes are rotated in such a way that the connecting lines of their anode contacts and cathode contacts extend at such an angle to the supply busbars that the anode contacts are situated above a first one of the supply busbars and the cathode contacts are situated above the second one of the supply busbars, and heat-dissipating contacts are situated to the side of the supply busbars.

* * * * *

UNITED STATES PATENT AND TRADEMARK OFFICE

CERTIFICATE OF CORRECTION

PATENT NO. : 7,910,899 B2
APPLICATION NO. : 11/547439
DATED : March 22, 2011
INVENTOR(S) : Platsch It is certified that error appears in the above-identified patent and that said Letters Patent is hereby corrected as shown below:

| | |
|---|---|
| Claim 23, Column 16, Line 16 | Replace “1” with “22” – “The light source of claim [[1]]22, wherein groups of light” |
| Claim 26, Column 16, Line 26 | Delete “carries” – “and carrying ~~carries~~ two supply busbars parallel to one” |
| Claim 65, Column 16, Line 47 | Delete “carries” – “and carrying ~~carries~~ two supply busbars parallel to one” |

Signed and Sealed this
Third Day of May, 2011

David J. Kappos

*Director of the United States Patent and Trademark Office*